US009264801B2

(12) United States Patent
Contolini et al.

(10) Patent No.: US 9,264,801 B2
(45) Date of Patent: Feb. 16, 2016

(54) SYSTEM AND METHOD FOR PAIRING A COMMAND DEVICE INCORPORATING A MICROPHONE TO A REMOTELY CONTROLLED MEDICAL SYSTEM

(71) Applicant: Storz Endoskop Produktions GmbH, Tuttlingen (DE)

(72) Inventors: Matteo Contolini, Goleta, CA (US); Ted H. Applebaum, Goleta, CA (US)

(73) Assignee: Storz Endoskop Produktions GmbH, Tuttlingen (DE)

( * ) Notice: Subject to any disclaimer, the term of this patent is extended or adjusted under 35 U.S.C. 154(b) by 461 days.

(21) Appl. No.: 13/693,801

(22) Filed: Dec. 4, 2012

(65) Prior Publication Data
US 2014/0153747 A1 Jun. 5, 2014

(51) Int. Cl.
*G06F 19/00* (2011.01)
*H04R 3/00* (2006.01)
*A61B 17/00* (2006.01)
*G10L 15/22* (2006.01)

(52) U.S. Cl.
CPC *H04R 3/00* (2013.01); *A61B 17/00* (2013.01); *G06F 19/34* (2013.01); *G06F 19/3406* (2013.01); *G06F 19/3418* (2013.01); *A61B 2017/00203* (2013.01); *G10L 2015/223* (2013.01)

(58) Field of Classification Search
CPC .. G06F 19/34; G06F 19/3406; G06F 19/3418
USPC ................................................. 704/231–257
See application file for complete search history.

(56) References Cited

U.S. PATENT DOCUMENTS

| | | | |
|---|---|---|---|
| 6,449,496 B1* | 9/2002 | Beith et al. | 455/563 |
| 6,928,490 B1 | 8/2005 | Bucholz et al. | |
| 6,959,260 B2* | 10/2005 | Rodman et al. | 702/150 |
| 7,620,553 B2 | 11/2009 | Wang et al. | |
| 8,344,847 B2* | 1/2013 | Moberg et al. | 340/3.2 |
| 2003/0223363 A1* | 12/2003 | Sato | 370/230 |
| 2005/0114140 A1 | 5/2005 | Brackett et al. | |
| 2006/0147055 A1* | 7/2006 | Ise | 381/95 |
| 2006/0282649 A1* | 12/2006 | Malamud et al. | 712/26 |
| 2008/0287062 A1* | 11/2008 | Claus et al. | 455/41.2 |
| 2009/0080348 A1* | 3/2009 | Hamel et al. | 370/310 |

(Continued)

FOREIGN PATENT DOCUMENTS

EP 2298178 A1 3/2011

OTHER PUBLICATIONS

European Search Report Application No. EP 13 19 5761 Completed: Feb. 14, 2014; Mailing Date: Feb. 26, 2014 3 pages.

*Primary Examiner* — Samuel G Neway
(74) *Attorney, Agent, or Firm* — Whitmyer IP Group LLC

(57) ABSTRACT

The system includes a remotely controlled medical system having a controller in communication with a command device incorporating a microphone. The system further includes a medical device operable by the controller and a sound generator coupled to the controller. The command device incorporating a microphone is paired to the controller for operating the medical device by detecting the sound. The command device incorporating a microphone transmits a signal in response to the sound to the controller to verify the pairing of the command device incorporating a microphone to the controller such that the controller will only operate the medical device in response to a command issued near the sound generator.

12 Claims, 7 Drawing Sheets

(56) References Cited

U.S. PATENT DOCUMENTS

| | | | |
|---|---|---|---|
| 2009/0121865 A1* | 5/2009 | Hamel et al. | 340/539.17 |
| 2009/0300507 A1* | 12/2009 | Raghavan et al. | 715/738 |
| 2011/0051016 A1* | 3/2011 | Malode | 348/734 |
| 2011/0053558 A1 | 3/2011 | Teague | |
| 2011/0063429 A1* | 3/2011 | Contolini et al. | 348/77 |
| 2011/0195632 A1* | 8/2011 | Chow | 446/397 |
| 2014/0153747 A1* | 6/2014 | Contolini et al. | 381/122 |

\* cited by examiner

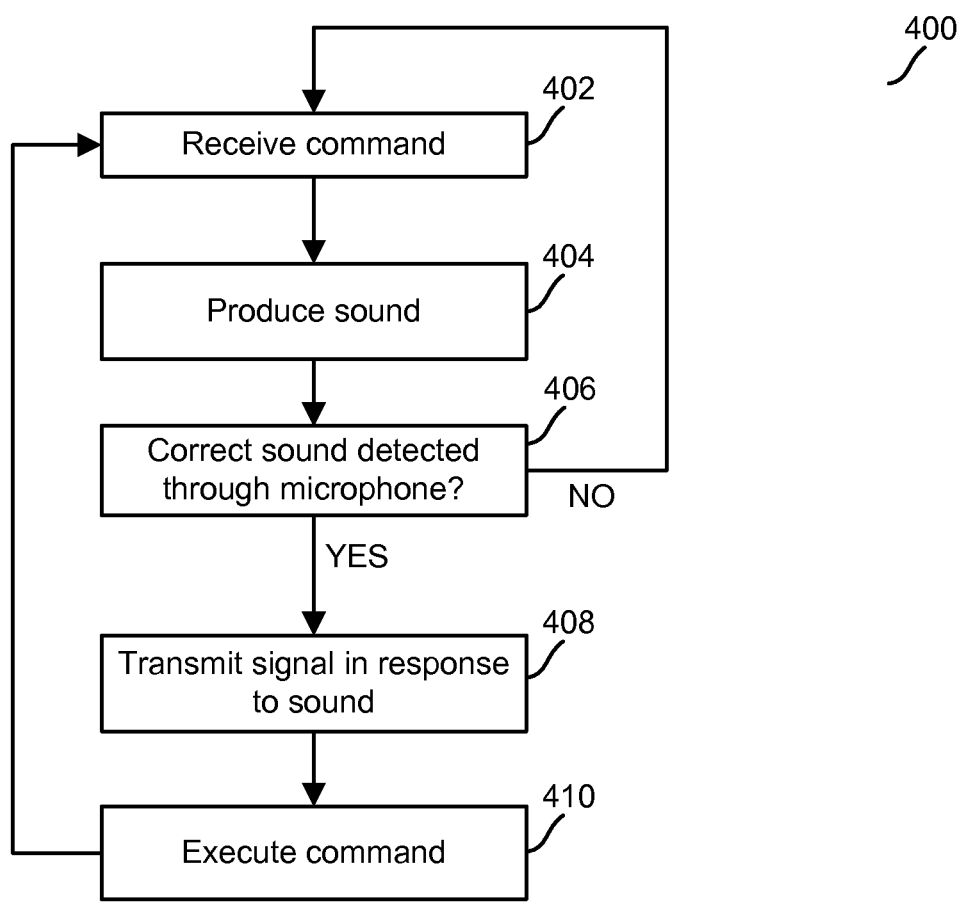

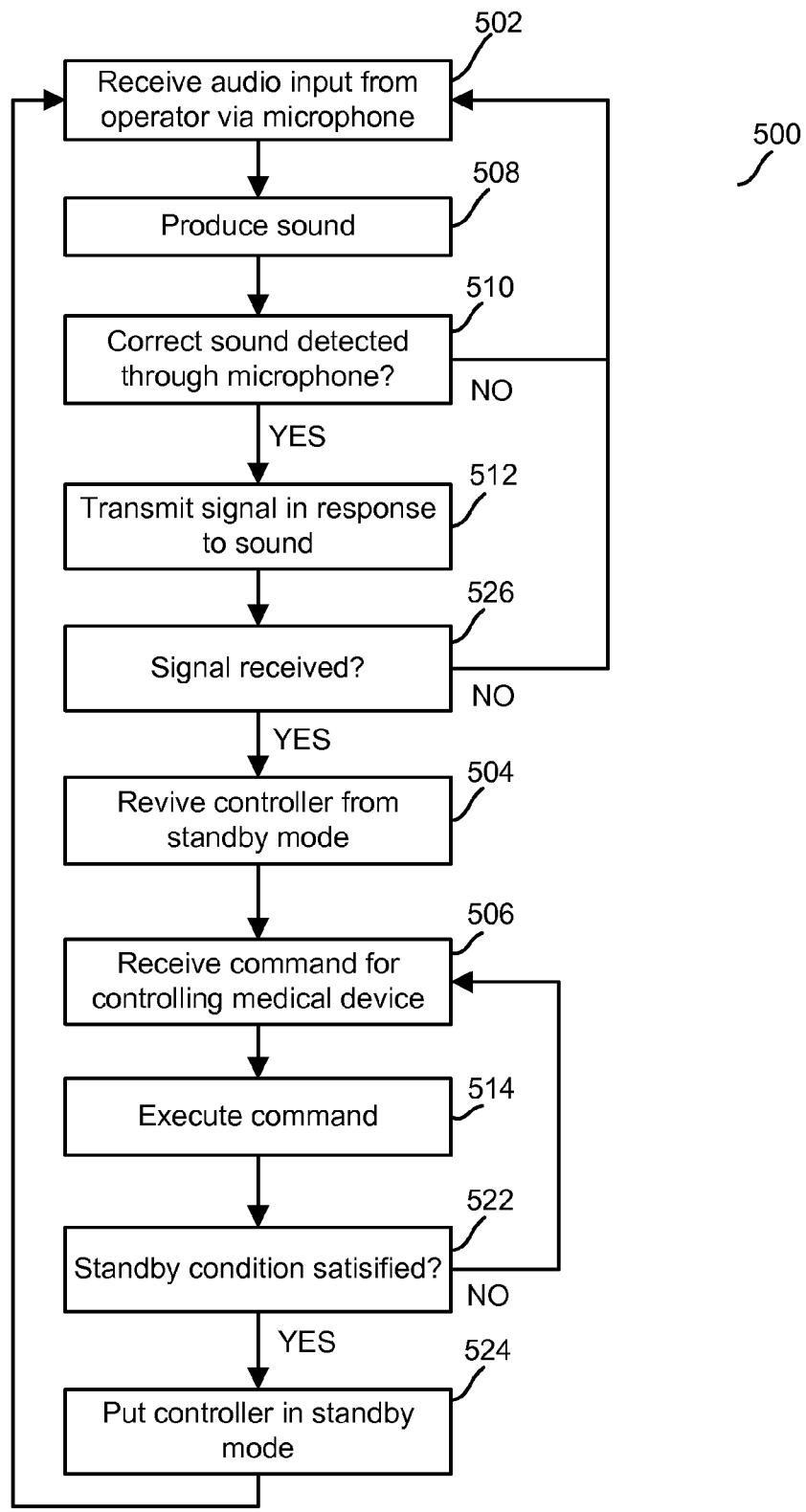

SYSTEM AND METHOD FOR PAIRING A COMMAND DEVICE INCORPORATING A MICROPHONE TO A REMOTELY CONTROLLED MEDICAL SYSTEM

FIELD OF THE INVENTION

The apparatus described herein generally relates to the field of remotely controlled digital operating rooms; and, more directly, to the field of safety systems for such operating rooms.

BACKGROUND OF THE INVENTION

Modern operating rooms for performing surgery have seen several advancements over the past two decades. In the late $20^{th}$ century, state-of-the-art operating rooms included several electronic surgical instruments (i.e. electrosurgical units, insufflators, endoscopes etc.). These instruments were separately operated by the surgeon and members of the surgical team. The industry improved upon this type of operating room by integrating the various instruments into a unified system. With this setup, the surgeon and/or members of the team use a central controller (or surgical control unit) to control all of the instruments through a single interface (preferably a graphical-user interface). Generally speaking, these central control units were built using modified personal computers and the operating rooms that use them are commonly referred to as "digital operating rooms".

The establishment of the digital operating room paved the way for the voice controlled operating room. With this system, a member of the surgical team (usually the surgeon) wears a headset with a microphone. The surgeon issues spoken commands into the headset, these commands are sent to the central controller which controls the various instruments to perform desired tasks or make on-the-fly adjustments to operating parameters. The central controller operates software including a speech-to-text converter to interpret and execute the voice commands. Since computers often have difficulty understanding spoken language, typical systems include audible confirmation feedback to the surgical team, notifying them that a command has been understood and executed by the controller. Since sterility is critically important in all surgical procedures, this touch-free control system represented a significant advancement.

The voice-controlled digital operating room was further improved by the introduction of the wireless voice-control headset. This gave the surgeon greater mobility and eliminated the microphone cable as a possible source of contamination or nuisance for the surgeon. The wireless revolution also ushered in the use of wireless input devices such as smart phones and tablets in digital operating rooms. Using one of these systems, a member of the surgical team can remotely control the digital operating room by manually entering commands into the wireless input device (i.e. a tablet) which the wireless input device then transmits to the central control unit. Voice controlled digital operating rooms with wireless headsets and wireless input devices represent the modern state-of-the-art in the field.

Although this type of system has worked well for the convenience and efficacy of the surgical team and the maintenance of sterility, it has introduced certain heretofore unknown safety issues. One such safety issue is the problem of surgeons issuing commands into wireless headsets and input devices that are mated with a nearby room's surgical control unit. In that situation, a surgeon may attempt to control a surgical control unit present in the room they are occupying, only to inadvertently control another surgical control unit in a nearby room where an unrelated procedure is being performed. This problem is exacerbated by the fact that a surgeon may repeat commands in a vain attempt to operate the surgical control unit in the room they are occupying. This can result in injury to the patient and surgical team and/or damage to the equipment in the nearby room.

There remains a need in the art for a safety system that prevents the inadvertent control of surgical control units with wireless voice-control headsets and wireless input devices.

SUMMARY OF THE INVENTION

A command device incorporating a microphone may be a microphone and wireless transmitter, a tablet or cell phone incorporating a microphone, a tablet with external (wired or Bluetooth) microphone, or a wireless headset with a microphone. A command device incorporating a microphone could also be one of several other systems not included on that list.

A system for pairing a command device incorporating a microphone to a remotely controlled medical system includes a controller in communication with a command device incorporating a microphone. The system further includes a medical device operable by the controller and a sound generator coupled to the controller. The command device incorporating a microphone is paired to the controller for operating the medical device by producing the sound. The command device incorporating a microphone transmits a signal to the controller in response to the sound to verify the pairing of the microphone to the controller such that the controller will only operate the medical device in response to a command issued near the sound generator.

A method of pairing a command device incorporating a microphone to a remotely controlled medical system includes receiving a command for controlling a medical device and producing a sound. The method further includes detecting the sound through the microphone and transmitting a signal in response to the sound. The method further includes executing the command to control the medical device only upon receiving the signal.

A method of pairing a command device incorporating a microphone to a remotely controlled medical system includes receiving an audio input from a user via the microphone, producing a sound and reviving a controller from a standby mode. The method further includes receiving a first command for controlling a medical device and producing a sound. The method further includes detecting the sound through the microphone and transmitting a signal in response to the sound. The method further includes executing the first command to control the medical device only upon receiving the signal. The method further includes receiving a subsequent command for controlling the medical device and executing the subsequent command to control the medical device. The method further includes repeating the steps in the previous sentence. The method further includes putting the controller in standby mode after a standby condition is satisfied. The standby condition may be one of: a pre-determined number of voice commands being rejected, a period of elapsed time when no audio input is received, or a user specifically commanding controller 150 to enter standby mode, or controller 150 automatically entering standby mode (e.g. during a phone call).

BRIEF DESCRIPTION OF THE DRAWINGS

FIG. 4 is a method of controlling a surgical system wherein a sound is used to confirm each command employable by the embodiment shown in FIG. 1.

FIG. 5 is a method of controlling a surgical system wherein a sound is used to confirm a sequence of commands employable by the embodiment shown in FIG. 1.

DETAILED DESCRIPTION OF THE INVENTION

Figure 1A:
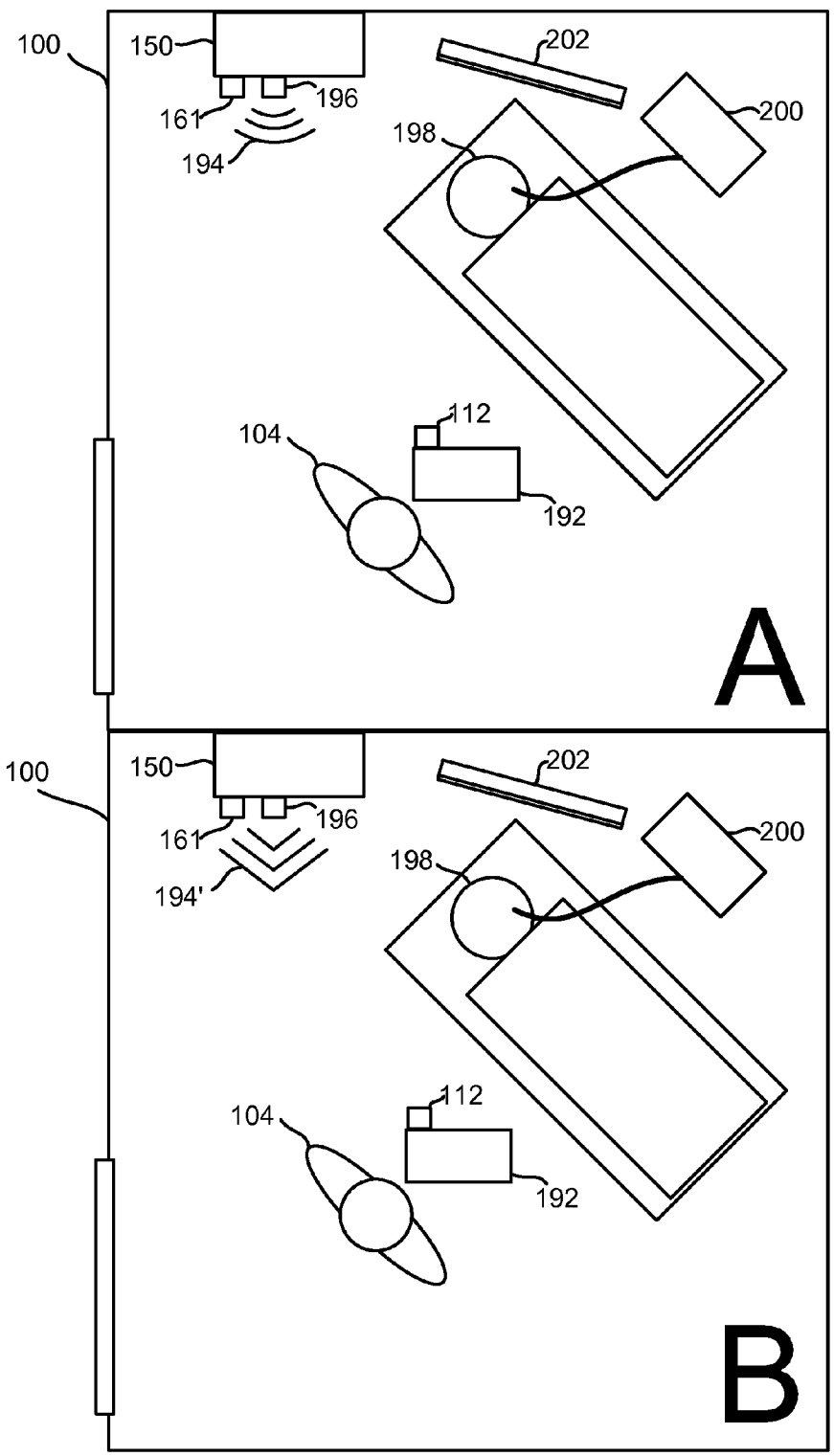
FIG. 1A is a top view of two adjacent operating rooms with active procedures being performed using one embodiment of the surgical system described herein.

FIG. 1A shows an embodiment of the system described herein being used in an operating room 100. FIG. 1A shows two adjacent operating rooms 100 (labeled A and B) where simultaneous surgical procedures are being performed by operators 104 on patients 198. Both operators 104 are using remotely controlled digital operating rooms 100. Operating rooms 100 are centrally controlled by controllers 150. Operator 104 issues commands via hand gestures, touch, or voice into input device 192 to control medical device 200 in the operating room. Medical device 200 is being used to perform a medical procedure on patient 198. Digital commands are transmitted from input device 192 to control module 161 on controller 150. Controller 150 and/or control module 161 controls medical device 200 by executing the commands. Usually, visual and audio feedback is given to operator 104 via display 202 and generator 196. Additional audio feedback is also given to operator 104 in the form of a verification sound 194 from sound generator 196, which is coupled to controller 150. Microphone 112 on input device 192 will detect verification sound 194 if operator 104 and microphone 112 are sufficiently close to sound generator 196 (i.e. in the same room).

Figure 1B:
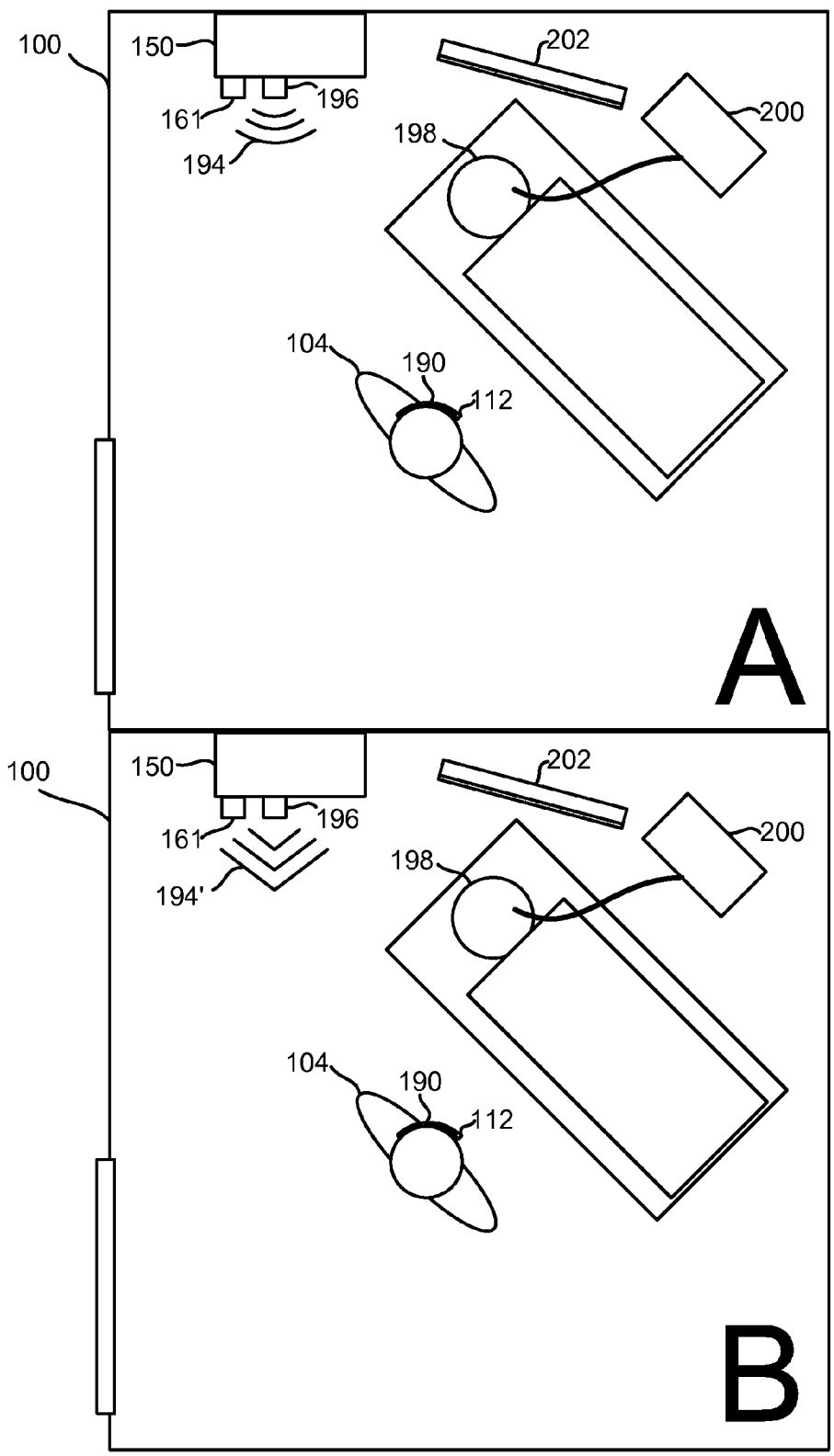
FIG. 1B is a top view of two adjacent operating rooms with active procedures being performed using one embodiment of the surgical system described herein.

FIG. 1B shows an embodiment of the system described herein being used in an operating room 100. FIG. 1B shows two adjacent operating rooms 100 (labeled A and B) where simultaneous surgical procedures are being performed by operators 104 on patients 198. Both operators 104 are using remotely controlled digital operating rooms 100. Operating rooms 100 are centrally controlled by controllers 150. Operator 104 issues spoken commands into microphone 112 to control medical device 200 in the operating room. Medical device 200 is being used to perform a medical procedure on patient 198. In this embodiment, microphone 112 is part of a wireless voice control headset 190. The commands are transmitted from microphone 112 to control module 161 on controller 150. Controller 150 and/or control module 161 interprets the commands and controls medical device 200 by executing the commands. Usually, visual and audio feedback is given to operator 104 via display 202 and generator 196. Additional audio feedback is also given to operator 104 in the form of a verification sound 194 from sound generator 196, which is coupled to controller 150. Microphone 112 will detect verification sound 194 if operator 104 and microphone 112 are sufficiently close to sound generator 196 (i.e. in the same room).

In FIGS. 1A and 1B, there could be the risk of controller 150 in operating room A receiving and executing commands from operator 104 in operating room B. This would pose a hazard to the equipment (i.e. medical device 200) and patient 198. However, this situation is avoided because each controller 150 will not execute commands unless it detects its unique verification sound 194. In FIGS. 1A and 1B, verification sound 194 is the unique verification sound for controller 150 in operating room A, whereas verification sound 194' is the unique verification sound for controller 150 in operating room B. As shown in FIGS. 1A and 1B, the two verification sounds 194, 194' are different wave forms.

In some systems, each headset 190 is permanently paired to a given controller 150 or voice control unit 161 and stored at a central location in a hospital. Operator 104 can either pick up the wrong headset 190 from the central repository or walk from one operating room 100 to another between procedures while retaining the same headset 190. Thus the risk arises that operator 104 will enter an operating room 100 (i.e. operating room A) with the headset 190 that is paired with the controller 150 in another operating room 100 (i.e. operating room B). In that type of system, verification sound 194 need not be unique for each controller 150, because the headsets 190 will already be in communication with only one controller 150. The only verification that needs to occur is that headset 190 must be close enough to detect the audio output of sound generator 196.

This is also the case for accessory input devices 192—they may be previously paired to a given controller 150, and only need to be verified by detecting verification sound 194. Further, requiring unique verification sounds 194 in each operating room 100 prevents a situation where multiple command devices paired to different operating rooms are in the same operating room and somehow pick up the same input command.

It is important to note that the verification sound or the term sound can mean any pressure disturbance in the room generated by sound generator 196. For example, verification sound 194, 194' can be any type of waveform or combination of waveforms, disturbances, tones, or noises, and may be audible or inaudible to human beings. In one embodiment verification sound 194 is a beep. For example, each controller 150 or control module 161 could have a beep with a different tone as its unique verification sound 194. Thus, each controller 150, headset 190, or input device 192 would listen for its unique tone before sending a verification signal and/or executing a command from operator 104. In another embodiment, verification sound 194 is a sequence of tones or a chord. In yet another embodiment, verification sound 194 is a recorded human voice or simulated human voice.

Verification sound 194 may be chosen to be easily and reliably distinguished from environmental noise, speech sounds or verification sounds 194' associated with other controllers 150. Verification sound 194 may further be chosen to be pleasant or unobjectionable to listeners. Verification sound 194 may be chosen to be in the range of human hearing or in a high frequency ultrasound range to avoid annoying listeners. The temporal trajectory of verification sound 194 may be tapered, with smooth onset and offset to avoid impulsive noise which is objectionable and difficult to analyze. Prominent frequencies in verification sound 194 may be chosen to match the preferential frequencies of a sound analysis system, such as the bin center frequencies of a Fast Fourier Transform used in a speech recognition system.

Identification of verification sound 194 may depend on multiple factors including temporal trajectory and duration of acoustic energy, overall acoustic energy, frequency structure and relative energy in different regions of the frequency spectrum. Reliability of verification sound identification may be enhanced by including redundant identifying information such as by using rich harmonic frequency content, or requiring detection of a sequence of sounds which follow a particular pattern. Robustness to identification failures may be obtained by smoothing the acceptance criteria: for example by accepting verification sound 194 even if criteria fall below otherwise acceptable levels for short intervals within the sounds. Thresholds for acceptance criteria may be dynamically adjusted using the behavior of operator 104 as corrective feedback. For instance if operator 104 cancels an accepted command, threshold for acceptance criteria may be made more stringent. Conversely, if operator 104 does not cancel a command which barely exceeded the criteria, those thresholds may be made more lenient.

Furthermore, it is also possible to calibrate the volume of verification sound 194 for optimal function—loud enough that it can be detected by microphone 112 in the appropriate operating room while not being loud enough to be inadvertently detected elsewhere in the building. The volume of verification sound 194 may also be calibrated to be within a comfortable hearing range for occupants of operating room 100—loud enough to be heard but not so loud as to cause discomfort or hearing damage.

The optimal sound level for verification sound 194 depends on multiple factors including the size and shape of operating room 100, noise level in operating room 100 and distance to other operating rooms. The verification sound level can be initially configured when system 300 is installed, based on algorithmic methods such as automatically adjusting the sound level until test instances of verification sound 194 are reliably identified, and/or based on the judgment of an installation technician. Support for calibration of the verification sound level may include triggering test instances of verification sound 194, an indication of whether verification sound 194 was identified, automatic increment or decrement of sound level and collection and display of the frequency of verification sound identification at various sound levels. Such support may be included in the system 300, or be part of a separate calibration kit used by the installation technician. Algorithmic or manual adjustment of sound level may be supported during the ordinary operation of system 300 to adapt to changing conditions.

It is also possible to have microphone 112 coupled with an input device 192, such as a wireless tablet. In that case, input device 192 and wireless headset 190 must be paired with controller 150 in order for controller 150 to execute commands from those devices. Operator 104 can execute commands via input device 192 by first sending a command through the communication channels between tablet 192 and controller 150. Controller 150 will receive the command and command sound generator 196 to generate verification sound 194. Microphone 112 on input device 192 will detect verification sound 194 and input device 192 and/or microphone 112 will send a signal to controller 150. Controller 150 will then execute the desired command and control medical device 200 as desired by operator 104. It is important to note that the verification signal being sent from microphone 112, input device 192, or wireless headset 190 may be any signal, including a facsimile or representation of verification sound 194.

If input device 192 is a tablet or has a graphical display, it could be paired with controller 150 by operator 104 using software installed on input device or tablet 192. For example, a user could press a button on tablet 192 or on its GUI, and begin a pairing process with controller 150. The user (via tablet 192 or otherwise) will put controller 150 into a pairing mode and put tablet 192 into a pairing mode. Tablet 192 will detect verification sound 194 and will compare it with a lookup table to determine the corresponding operating room 100. Tablet 192 will transmit the appropriate pairing and logon instructions to be validated by controller 150. Operator 104 can then use tablet 192 to control medical device 200 via controller 150.

Medical device 200 may be any type of surgical device, bedside life support device, or any other medical device that can be controlled by controller 150. For example medical device 200 may be an insufflator, a suction device, a light source, a video camera, a pressure gauge, a pump, an electrosurgical unit, a surgical table, a room camera, a room light, or an endoscope. Furthermore it is possible that multiple medical devices 200 will be operated by one controller 150 and any given command from operator 104 may be intended for one or more devices 200.

Figure 2:
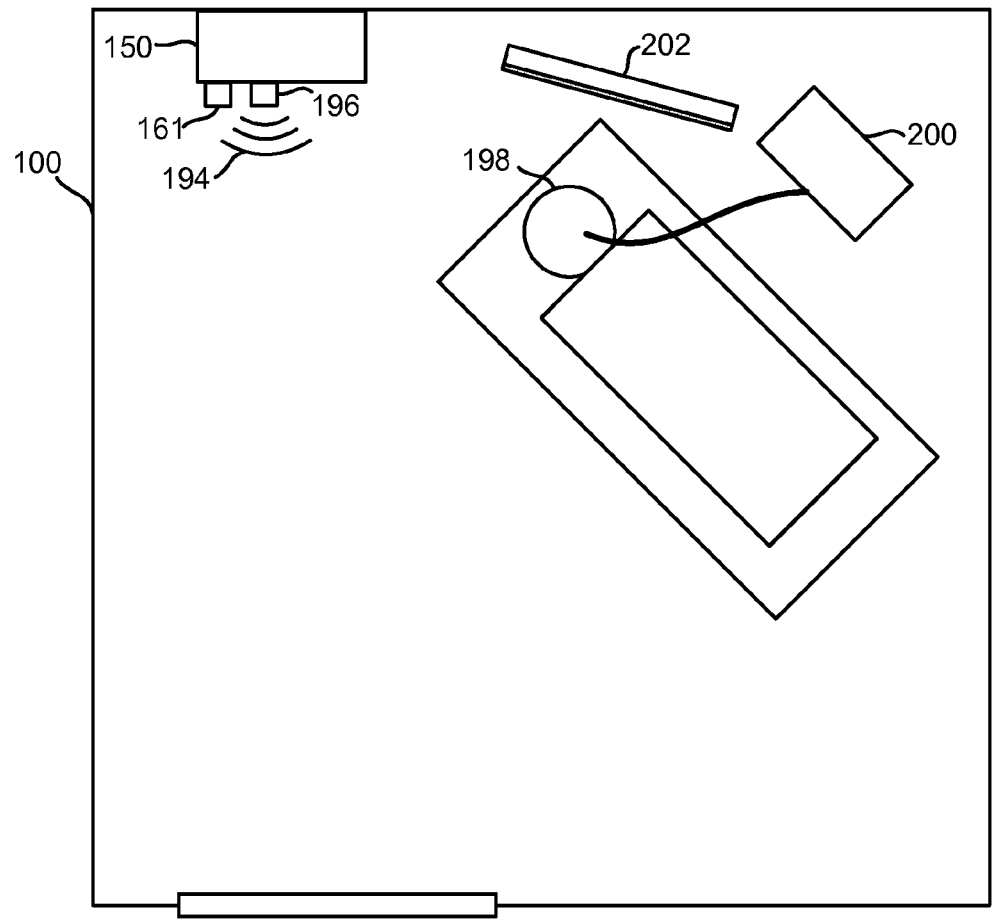
FIG. 2 is a top view of an operating room including one embodiment of the surgical system and an operator outside of the operating room.
Figure 2:
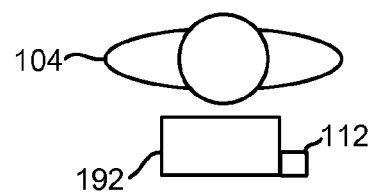

In FIG. 2 operator 104 has left operating room 100 but is still carrying input device 192. There is a risk in this situation that operator 104 could inadvertently issue commands to controller 150. These commands could be executed on medical device 200 and could injure patient 198. In FIG. 2, operator 104 may issue an unwanted command on the system described herein. However, sound generator 196 will generate a verification sound 194 in response to the command. Since microphone 112 is outside of operating room 100 in FIG. 2, verification sound 194 will not transmit through the walls of operating room 100 to a significant degree. Therefore, microphone 112 will not detect verification sound 194 and controller 150 will not execute the operator's 104 inadvertent command, preventing injury to patient 198 or damage to medical device 200 or other equipment in operating room 100.

Figure 3A:
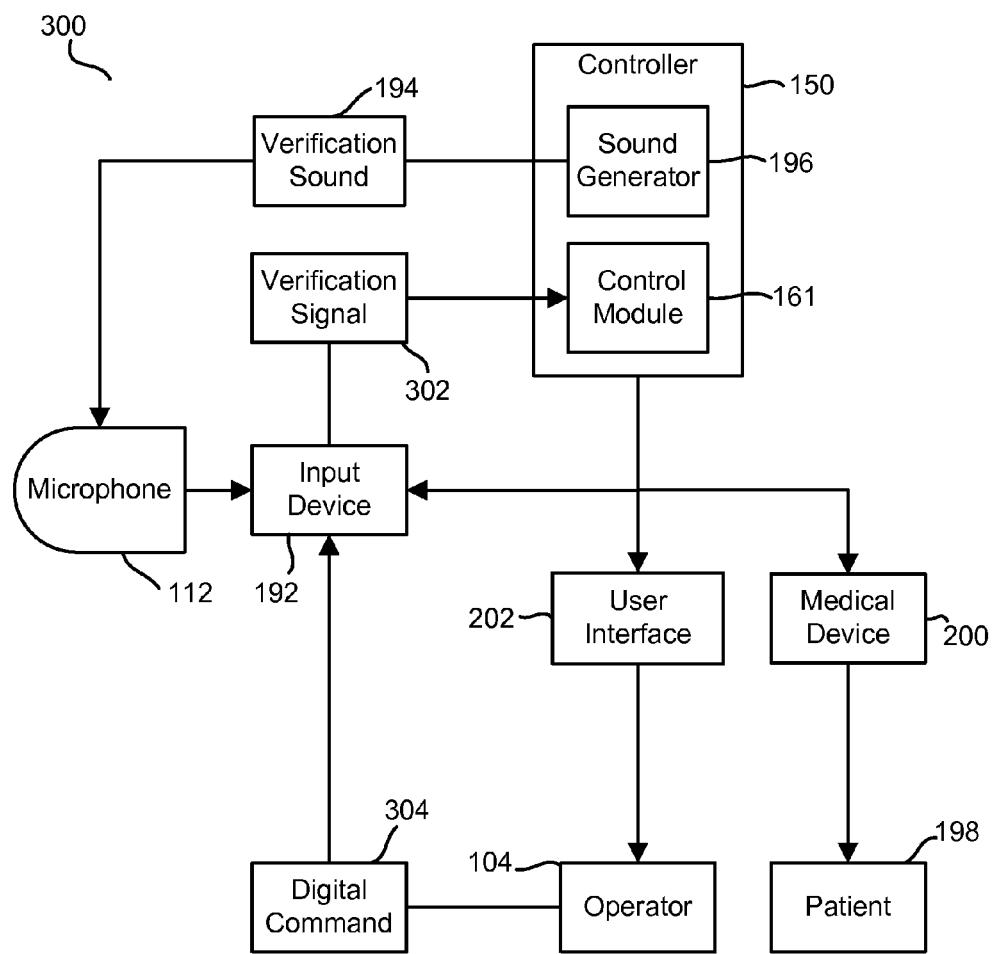
FIG. 3A is a diagram illustrating one embodiment of the surgical system.

FIG. 3A is a diagram of one embodiment of the voice controlled medical system 300. Operator 104 enters digital commands 304 (as indicated by box 304 and the dashed line) through input device 192. Controller 150 comprises sound generator 196 that generates verification sound 194. This sound 194 is received by microphone 112 and identified by input device 192 or controller 150. Input device 192 is then prompted to send verification signal 302 to control module 161 and/or controller 150. Controller 150 then sends data to user interface 202 or input device 192 to provide information to operator 104 and executes commands 304 by sending instructions to medical device 200 which operates on patient 198. Medical device 200 could be an insufflator, a suction device, a pressure gauge, a pump, an electrosurgical unit, a surgical table, or an endoscope. Medical device 200 could also be a device that does not directly operate on patient 198, such as a light source, a video camera, personal digital assistant, or a telephone. Verification sound 194 can be analyzed for matching identification by controller 150, or input device 192. If verification sound 194 is verified by input device 192, those devices may send a signal other than verification sound 194 itself to controller 150 to authorize the execution of digital command 304.

Figure 3B:
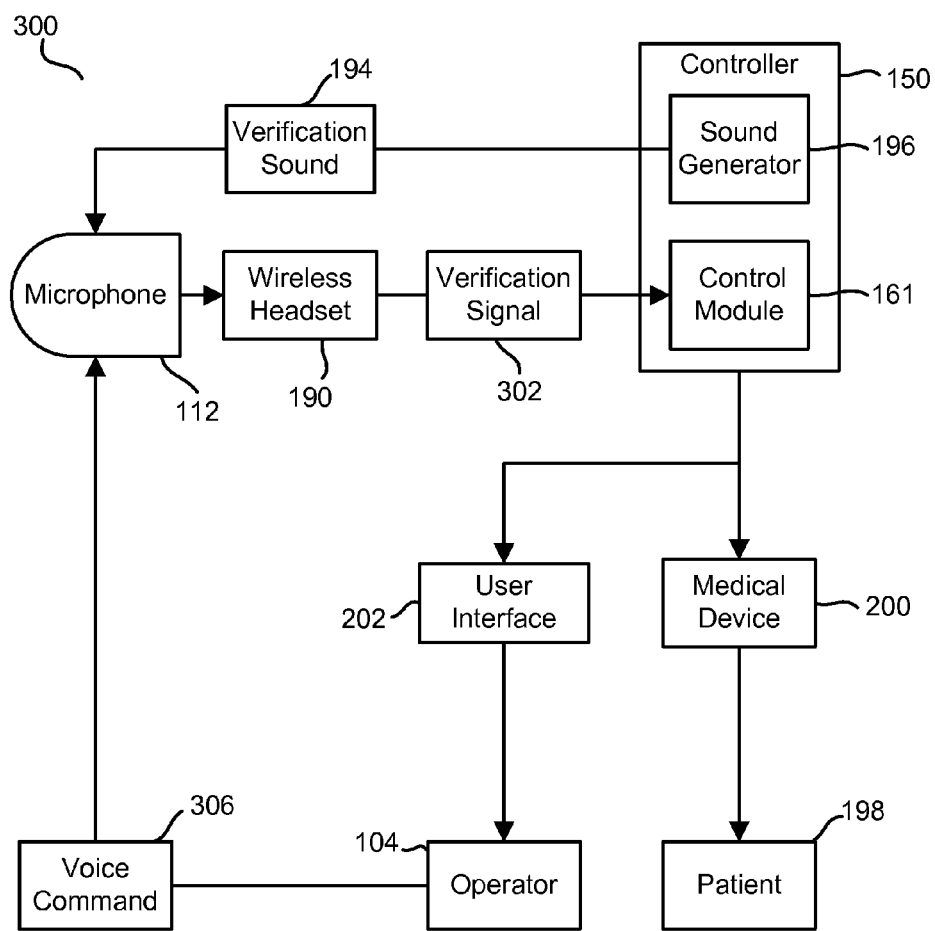
FIG. 3B is a diagram illustrating one embodiment of the surgical system.

FIG. 3B is a diagram of one embodiment of the voice controlled medical system 300. Operator 104 enters voice commands 306 (as indicated by box 306 and the dotted line) through microphone 112. Controller 150 comprises sound generator 196 that generates verification sound 194. This sound is detected by microphone 112 which prompts wireless headset 190 to send verification signal 302 to control module 161 and/or controller 150. Controller 150 then sends data to user interface 202 or input device 192 to provide information to operator 104 and executes voice commands 306 by sending instructions to medical device 200 which operates on patient 198. Medical device 200 could be an insufflator, a suction device, a pressure gauge, a pump, an electrosurgical unit, a surgical table, or an endoscope. Medical device 200 could also be a device that does not directly operate on patient 198, such as a light source, a video camera, personal digital assistant, or a telephone. Verification sound 194 can be analyzed for matching identification by controller 150 or headset 190. If verification sound 194 is verified by headset 190, that device may send a signal other than verification sound 194 itself to controller 150 to authorize the execution of voice command 306.

FIG. 4 is a diagram of a method 400 according to one embodiment. The method includes the steps of receiving a command 402, producing a sound 404, determining if the correct sound was detected through the microphone 406, transmitting a signal in response to the sound if the correct sound is detected 408, and executing a command to control a medical device 410.

FIG. 5 is a diagram of a second method 500 according to one embodiment. The method includes the steps of receiving audio input from an operator via a microphone 502, producing a sound 508, determining if the correct sound has been detected through the microphone 510, transmitting a signal in response to the sound if the correct sound is detected 512, determining if the signal is received 526, reviving a controller from standby mode if the signal is received 504, receiving a command for controlling a medical device 506, executing a command to control a medical device upon receiving the signal 514, determining if a standby condition is satisfied (for example, waiting for a period when no audio input is received) 522 and putting the controller in standby mode if a standby condition is satisfied 524. The process is restarted when an audio input is received again (step 502).

Thus, it is appreciated from FIG. 4 that controller 150 may require detection of verification sound 194 before executing any command 304, 306. In that situation, controller 150 may simply use a feedback noise normally used to alert operator 104 that command 304, 306 has been understood as verification sound 194. In that embodiment, operator 104 issues command 304, 306 and if controller 150 understands command 304, 306, it generates command verification sound 194 to alert operator 104 that command 304, 306 is recognized. Controller 150 then listens for its own verification sound 194 through microphone 112 and only executes command 304, 306 upon detecting verification sound 194 through microphone 112.

In another embodiment (as shown in FIG. 5), controller 150 normally remains in a standby or sleep mode. Operator 104 awakens controller 150 by issuing a general input (audio or otherwise), a command 304, 306 (for medical device 200 or a wakeup command), or a password or pass key, to controller 150. This can be accomplished through microphone 112 on headset 190 or input device 192. Controller 150 will then generate verification sound 194. Upon detecting verification sound 194 through microphone 112, controller 150 will enter an awake or operational mode. Controller 150 will then either execute command 304, 306 it has just received from operator 104, or it will await a new command 304, 306.

Once in the awake or operational mode, controller 150 will execute commands 304, 306 (with or without continuing to generate a verification noise 194 after recognizing valid commands 304, 306) without conditioning the execution of the commands on detecting a verification signal 302 or verification noise 194. In other words, once out of standby mode, controller 150 will execute any commands it receives because the source (headset 190 or input device 192) has already been verified as being in the vicinity of controller 150. This is more convenient for operator 104 because there is less likelihood of delays associated with commands 304, 306 failing to be executed because of a failure to verify them with verification sound 194. In one embodiment (such as the one shown in FIG. 4), once a surgical procedure is over, there will be a period when controller 150 receives no input or commands from microphone 112, headset 190, or input device 192. After a set time has elapsed (a timeout period), controller 150 will re-enter standby mode. However, in other embodiments timeouts will be more frequent and controller 150 will enter standby mode one or more times during a surgical procedure. In other embodiments, standby mode will be re-entered after a standby condition is satisfied, such as a pre-determined number of voice commands being rejected or a user specifically commanding controller 150 to enter standby mode.

In another embodiment (such as the one shown in FIG. 5), controller 150 only checks verification sound 194 after critical or hazardous commands. Thus, for some commands controller 150 will execute command 304, 306 without first verifying proximity. If command 304, 306 is critical or could be hazardous to patient 198 or medical device 200, controller 150 will only execute command 304, 306 upon detecting verification sound 194. For example, if command 304, 306 is for an insufflator which could injure patient 198, the controller may consider command 304, 306 to be critical.

The systems and methods described herein successfully prevent accidents by using sounds to pair command devices incorporating microphones to remotely controlled medical systems. This is accomplished by using sounds to verify the proximity of the command device to the sound generator and takes advantage of the attenuation of sound in air over distance and the relatively poor transmission of sound through solid barriers compared to uninterrupted air.

Although the invention has been described with reference to embodiments herein, those embodiments do not limit the scope of the invention. Modifications to those embodiments or different embodiments may fall within the scope of the invention.

What is claimed is:

1. A system for pairing a command device incorporating a microphone to a remotely controlled medical system, comprising:
   a command device incorporating a microphone;
   a controller in communication with the command device incorporating a microphone;
   a medical device operable by the controller; and
   a generator coupled to the controller that generates a sound;
   said command device incorporating a microphone is paired to said controller for operating said medical device by:
      said generator producing said sound;
      said microphone transmitting a signal in response to the sound to said controller to verify the pairing of the microphone to the controller such that the controller will only operate the medical device in response to a command issued near the generator;
   an input device associated with the microphone that sends the command to the controller;
   software executing on said input device for detecting said sound;
   software executing on said input device for comparing said sound with a lookup table to determine a corresponding controller; and
   software executing on said input device for transmitting pairing and logon instructions to said corresponding controller.

2. The system of claim 1, wherein the sound is one of: a beep, a tone, a sequence of tones, a chord, a sequence of chords, a voice speech sound.

3. The system of claim 1, wherein the sound is unique to the controller in a particular operating room.

4. The system of claim 1, wherein the input device is one of: a tablet, a phone, a portable personal computer, or a dedicated remote control unit.

5. The system of claim 1, wherein the command device incorporating a microphone communicates with the controller wirelessly.

6. The system of claim 5, wherein the command device incorporating a microphone is a component of a wireless voice control headset.

7. The system of claim 1, wherein the command is a voice command spoken by a user and the sound is generated after the controller recognizes the command.

8. The system of claim 1, wherein the command is a digital command generated in response to one of: touching a button on the command device, or making a gesture on a touch screen on the command device.

9. The system of claim 1, wherein the medical device is an insufflator, a suction device, a light source, a video camera, a video control unit, a pressure gauge, a pump, an electrosurgical unit, a surgical table, a telephone, room lights, a personal digital assistant, a room camera, or an endoscope.

10. The system of claim 1, further comprising:
    software executing on said controller for calibrating the volume of said sound.

11. The system of claim 1, further comprising:
    software executing on said controller to determine the authenticity of the sound by evaluating it based on at least one criterion; and
    software executing on said controller to adjust the specificity of the evaluation.

12. The system of claim 3, wherein the sound has a unique wave form to the controller in a particular operating room.

* * * * *